US008981770B2

(12) United States Patent
Gleich

(10) Patent No.: US 8,981,770 B2
(45) Date of Patent: Mar. 17, 2015

(54) APPARATUS AND METHOD FOR INFLUENCING AND/OR DETECTING MAGNETIC PARTICLES

(75) Inventor: Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 386 days.

(21) Appl. No.: 13/384,636

(22) PCT Filed: Jul. 12, 2010

(86) PCT No.: PCT/IB2010/053182
§ 371 (c)(1),
(2), (4) Date: Jan. 18, 2012

(87) PCT Pub. No.: WO2011/010243
PCT Pub. Date: Jan. 27, 2011

(65) Prior Publication Data
US 2012/0146632 A1    Jun. 14, 2012

(30) Foreign Application Priority Data
Jul. 20, 2009 (EP) ...................................... 09165864

(51) Int. Cl.
*G01N 27/84* (2006.01)
*A61B 5/05* (2006.01)
(52) U.S. Cl.
CPC ................ *A61B 5/05* (2013.01); *A61B 5/0515* (2013.01)
USPC ........... 324/214; 324/201; 324/203; 324/224; 324/216; 600/407; 600/408; 600/424; 607/105
(58) Field of Classification Search
USPC ......... 324/201, 203, 214, 224, 216, 228, 244, 324/260–263, 301, 310, 318, 319; 600/407–411, 424–425
See application file for complete search history.

(56) References Cited

U.S. PATENT DOCUMENTS 5,136,242 A * 8/1992 Abraham-Fuchs ............ 324/244
5,239,591 A * 8/1993 Ranganath .................... 382/128
(Continued)

FOREIGN PATENT DOCUMENTS

CN    1180304 A     4/1998
CN    1882364 A    12/2006
(Continued)

OTHER PUBLICATIONS

Knopp T. et al. "Trajectory analysis for magnetic particle imaging". Physics in Medicine and Biology, Taylor and Francis Ltd., London, vol. 54, No. 2, Jan. 21, 2009, pp. 385-397.
(Continued)

*Primary Examiner* — Huy Q Phan
*Assistant Examiner* — Thang Le

(57) ABSTRACT

The present invention relates to an apparatus and a method for void size determination of voids within an object into which an aerosol containing magnetic particles has been introduced, in particular for determining the size of a patient's pulmonary alveoli, said patient having inhaled an aerosol containing magnetic particles To review information concerning the lung structure, it is proposed to use magnetic particle imaging. First and second detection signals are acquired subsequently at different moments in time after introduction of the aerosol containing the magnetic particles into the object, in particular after inhalation of the aerosol by the patient. These detection signals are exploited, in particular the drop in intensity and/or the signal decay time, to get information about the diffusion of the magnetic particles within the voids, in particular alveoli, and to retrieve information therefrom about the size of the voids, in particular alveoli.

12 Claims, 5 Drawing Sheets (Marked To Show Changes)

(56) References Cited

U.S. PATENT DOCUMENTS

| | | | |
|---|---|---|---|
| 5,309,106 A * | 5/1994 | Miyajima et al. | 324/318 |
| 5,353,795 A * | 10/1994 | Souza et al. | 600/423 |
| 6,997,863 B2 * | 2/2006 | Handy et al. | 600/9 |
| 7,463,024 B2 * | 12/2008 | Simola et al. | 324/247 |
| 8,480,406 B2 * | 7/2013 | Alexander et al. | 434/270 |
| 8,731,641 B2 * | 5/2014 | Hartmann et al. | 600/424 |
| 2003/0097068 A1 * | 5/2003 | Hossack et al. | 600/443 |
| 2005/0249667 A1 * | 11/2005 | Tuszynski et al. | 424/9.3 |
| 2006/0210986 A1 | 9/2006 | Gleich | |
| 2006/0211939 A1 | 9/2006 | Gleich | |
| 2006/0241376 A1 * | 10/2006 | Noble et al. | 600/410 |
| 2007/0253609 A1 | 11/2007 | Aben | |
| 2007/0258888 A1 | 11/2007 | Feldmann et al. | |
| 2012/0035438 A1 * | 2/2012 | Ferren et al. | 600/302 |

FOREIGN PATENT DOCUMENTS

| | | |
|---|---|---|
| DE | 10151778 A1 | 5/2003 |
| WO | WO9628090 | 9/1996 |
| WO | WO2005046733 | 5/2005 |

OTHER PUBLICATIONS

Weizenecker, J. et al., "Letter to the Editor: Three-dimensional real-time in vivo magnetic particle imaging". Physics in Medicine and Biology, Taylor and Francis Ltd. , London, vol. 54, No. 5, Mar. 7, 2009, pp. L1-L10.

Gleich, B. "Tomographic Imaging Using the Nonlinear Response of Magnetic Particles". Nature Publishing Group. vol. 435/50 Jun. 2005/doi:10.1038/nature03808, US.

S.G. Ruehm, et al., "Magnetic Resonance Imaging of Atherosclerotic Plaque with Ultrasmall Superparamagnetic Particles of Iron Oxide in Hyperlipidemic Rabbits", Circulation, Jan. 23, 2001, pp. 415-422.

* cited by examiner (Marked To Show Changes)

APPARATUS AND METHOD FOR INFLUENCING AND/OR DETECTING MAGNETIC PARTICLES

FIELD OF THE INVENTION

The present invention relates to an apparatus and a method for void size determination of voids within an object into which an aerosol containing magnetic particles has been introduced. The present invention particularly relates to an apparatus and a method for determining the size of a patient's pulmonary alveoli, said patient having inhaled an aerosol containing magnetic particles. Further, the present invention relates to a computer program for implementing said method on a computer and for controlling such an apparatus.

BACKGROUND OF THE INVENTION

Magnetic Particle Imaging (MPI) is an emerging medical imaging modality. The first versions of MPI were two-dimensional in that they produced two-dimensional images. Future versions will be three-dimensional (3D). A time-dependent, or 4D, image of a non-static object can be created by combining a temporal sequence of 3D images to a movie, provided the object does not significantly change during the data acquisition for a single 3D image.

MPI is a reconstructive imaging method, like Computed Tomography (CT) or Magnetic Resonance Imaging (MRI). Accordingly, an MP image of an object's volume of interest is generated in two steps. The first step, referred to as data acquisition, is performed using an MPI scanner. The MPI scanner has means to generate a static magnetic gradient field, called "selection field", which has a single field free point (FFP) at the isocenter of the scanner. In addition, the scanner has means to generate a time-dependent, spatially nearly homogeneous magnetic field. Actually, this field is obtained by superposing a rapidly changing field with a small amplitude, called "drive field", and a slowly varying field with a large amplitude, called "focus field". By adding the time-dependent drive and focus fields to the static selection field, the FFP may be moved along a predetermined FFP trajectory throughout a volume of scanning surrounding the isocenter. The scanner also has an arrangement of one or more, e.g. three, receive coils and can record any voltages induced in these coils. For the data acquisition, the object to be imaged is placed in the scanner such that the object's volume of interest is enclosed by the scanner's field of view, which is a subset of the volume of scanning.

The object must contain magnetic nanoparticles; if the object is an animal or a patient, a contrast agent containing such particles is administered to the animal or patient prior to the scan. During the data acquisition, the MPI scanner steers the FFP along a deliberately chosen trajectory that traces out the volume of scanning, or at least the field of view. The magnetic nanoparticles within the object experience a changing magnetic field and respond by changing their magnetization. The changing magnetization of the nanoparticles induces a time dependent voltage in each of the receive coils. This voltage is sampled in a receiver associated with the receive coil. The samples output by the receivers are recorded and constitute the acquired data. The parameters that control the details of the data acquisition make up the scan protocol.

In the second step of the image generation, referred to as image reconstruction, the image is computed, or reconstructed, from the data acquired in the first step. The image is a discrete 3D array of data that represents a sampled approximation to the position-dependent concentration of the magnetic nanoparticles in the field of view. The reconstruction is generally performed by a computer, which executes a suitable computer program. Computer and computer program realize a reconstruction algorithm. The reconstruction algorithm is based on a mathematical model of the data acquisition. As with all reconstructive imaging methods, this model is an integral operator that acts on the acquired data; the reconstruction algorithm tries to undo, to the extent possible, the action of the model.

Such an MPI apparatus and method have the advantage that they can be used to examine arbitrary examination objects—e.g. human bodies—in a non-destructive manner and without causing any damage and with a high spatial resolution, both close to the surface and remote from the surface of the examination object. Such an arrangement and method are generally known and are first described in DE 101 51 778 A1 and in Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication take advantage of the non-linear magnetization curve of small magnetic particles.

In lung imaging, there may be more relevant parameters then the pure ventilated air space. By use of MRI (Magnetic Resonance Imaging) and applying an appropriate MRI sequence the pulmonary diffusion coefficient can be determined, The diffusion parameters of gasses may reveal deeper insight into the structure of the lung revealing potentially important information for asthma, emphysema and chronic obstructive pulmonary disease. The apparent diffusion coefficient is linked to the average distance to the lung surface, thus a large diffusion indicates e.g. enlarged alveoli.

SUMMARY OF THE INVENTION

It is an object of the present invention to provide an alternative apparatus and method for void size determination of voids within an object into which an aerosol containing magnetic particles has been introduced.

It is particularly an object of the present invention to provide an apparatus and a method for determining the size of a patient's pulmonary alveoli, said patient having inhaled an aerosol containing magnetic particles, which apparatus and method enable to reveal information concerning the lung structure.

In a first aspect of the present invention an apparatus is presented comprising:

- selection means comprising a selection field signal generator unit and selection field generation elements for generating a magnetic selection field having a pattern in space of its magnetic field strength such that a first sub-zone having a low magnetic field strength and a second sub-zone having a higher magnetic field strength are formed in a field of view,
- drive means comprising drive field signal generator units and drive field coils for changing the position in space of the two sub-zones in the field of view by means of a magnetic drive field so that the magnetization of the magnetic material changes locally,
- receiving means comprising at least one signal receiving unit and at least one receiving coil for acquiring detection signals, which detection signals depend on the magnetization in the field of view, which magnetization is influenced by the change in the position in space of the first and second sub-zone, and
- processing means for determining for determining the void size of voids within the object from first detection signals acquired directly after introduction of the aerosol and second detection signals acquired after a time duration after introduction of the aerosol.

In a further aspect of the present invention a corresponding method is presented.

In still a further aspect of the present invention a computer program is presented comprising program code means for causing a computer to control the apparatus according to the present invention to carry out the steps of the method according to the present invention when said computer program is carried out on the computer.

Preferred embodiments of the invention are defined in the dependent claims. It shall be understood that the claimed method and the claimed computer program have similar and/or identical preferred embodiments as the claimed apparatus and as defined in the dependent claims.

The present invention is based on the idea to that MPI offers a possibility to reveal information concerning the lung structure or, more generally, about the size of voids existing within an object. Such a contrast can be based on the signal generation in the air space due to fast Brownian rotation mechanisms. In MPI, usually the Brownian rotation is excluded as an effective mechanism for signal generation in a liquid suspension. The viscosity of air is only 18 µPas leading to a more than 50 times the magnetization speed in water. Therefore, it is possible to efficiently detect magnetic particles in the air space, even if the anisotropy is so high that the Neel process is blocked.

When a magnetic particle reaches the lung's surface (more generally, the void's wall), the Brownian rotation is blocked and the MPI signal ("detection signal") vanishes. The magnetic particles will reach the lung surface (void's wall) by diffusion. The speed of the diffusion can be estimated using the Einstein formula $$x = \sqrt{\frac{2kTt}{3r\eta\pi}}.$$

where x is the mean travel distance, r the particles radius, η the viscosity of the medium, k the Boltzmann constant, T the absolute temperature and t the time. For instance, for air viscosity and 40 nm magnetic particle diameter, the mean travel distance x in one second is about 50 µm. This matches with the typical alveolar air space of typically 50 to 250 µm.

In emphysema, the air space is enlarged, which is detectable using MPI. For instance, in an embodiment, the signal decay time of the detection signals is exploited to get information about the size of the alveoli, which then allows determining whether or not there are any defects. Thus, generally, the size of the voids can be determined in an embodiment by exploiting the signal decay time of the detection signals.

Since the mean travel distance is rather short and since MPI is very fast in detecting the detection signals, it is generally not necessary to hold the breath for a longer time, e.g. for longer than 5 seconds.

The discussion above assumed magnetic particles with completely blocked Neel rotation. Nevertheless it is possible to exploit the detection signals, e.g. to use the change in signal shape as proposed in an embodiment, when magnetic particles with only slight anisotropy get attached to the lung (or void's) surface. Therefore, existing iron oxide nano-particles (e.g. Resovist) may be used for this evaluation. The magnetic particles are preferably sprayed to a fine aerosol and inhaled by the patient (or, generally, introduced into the object) prior to the application of the method according to the present invention, i.e. prior to application of the magnetic fields for acquiring detection signals.

To generate said aeorosol, an embodiment of the apparatus according to the present invention comprises an aerosol generator, in particular generating an aerosol with singularized magnetic particles.

According to the present invention first detection signals are acquired directly after inhalation/introduction of the aerosol and second detection signals are acquired after a time duration after inhalation/introduction of the aerosol, i.e. after the inhaled magnetic particles contained in the aerosol had some time to travel (i.e. diffuse) in the alveoli/voids.

When the magnetic particles have not yet reached the lung surface/void's wall (i.e. the surface of the alveolus/void in which they are travelling), their viscosity is comparably low so that a comparably high detection signal is acquired from those magnetic particles. However, when the magnetic particles have reached the lung surface/void's wall, their viscosity is comparably high so that a comparably low detection signal is acquired from those magnetic particles. Thus, from those first and second detection signals differences of the detection signals can be determined, provided the time gap between the acquisition of the first and second detection signals is long enough to allow the magnetic particles to travel a certain distance.

The invention can be applied for determining the size of voids of different sizes, including sizes below the resolution of the detection signals. If applied for determining the size of alveoli, the resolution of the detection signals is generally larger than the size of single alveoli. In such cases, a single voxel of an image reconstructed from the detection signals covers a group of alveoli.

Areas of application are, besides medical applications for determining the size of a patient's alveoli, production technologies, e.g. for determining the size of voids in a workpiece (e.g. a foam) to confirm that the mean size of voids is below a predetermined threshold or that a maximum size is not exceeded. Another application is to determine how compact a bulk good is packed, e.g. to find out if there are large unused areas in the packing.

The delay time between the acquisition of the first and second detection signals depends on the viscosity of the medium within the voids and the void size. For size measurements of alveoli, a typical delay time will be between 1 and 5 seconds. However, it is preferred to acquire more than two sets of detection signals at subsequent time intervals.

Preferably, in particular for determining the size of alveoli, the mean size of alveoli is determined. Depending on the area of the examined alveoli, a respective threshold value for the alveolus size is used to differentiate between healthy (small) and unhealthy (large) alveoli. This is required since the size and occurrence of alveoli varies within the lung. Such thresholds are generally obtained in advance, preferably for various diseases of the lung. The same holds generally for non-medical applications, where information about typical and non-typical void sizes is obtained for use in determining a typical threshold.

The invention can be applied for determining the size of voids of different sizes, including sizes below the resolution of the detection signals. If applied for determining the size of alveoli, the resolution of the detection signals is generally larger than the size of single alveoli. In such cases, a single voxel of an image reconstructed from the detection signals covers a group of alveoli. In an embodiment it is also possible to determine means values for the sizes over groups of alveoli. Preferably, the size determination is done for the complete lung, but also a restriction to certain areas is possible, e.g. if there areas are under suspect for comprising defective alveoli.

Areas of application are, besides medical applications for determining the size of a patient's alveoli, production technologies, e.g. for determining the size of voids in a workpiece (e.g. a foam) to confirm that the mean size of voids is below a predetermined threshold or that a maximum size is not exceeded. Another application is to determine how compact a bulk good is packed, e.g. to find out if there are large unused areas in the packing.

There are various possibilities available for determining void size of voids within the object, e.g. the size of alveoli within a patient's lung, from the first and second detection signals. According to one embodiment the void size of voids within the object is determined by comparing the first and second detection signals, in particular for predetermined areas in the field of view. From the determined difference, e.g. in the intensity of the signal decay and/or the signal decay time, as proposed according to further embodiments, information can be gained about the travelling time of the magnetic particles and/or an estimate of the percentage of magnetic particles that have attached to the lung (or object) surface after a certain period of time can be made, allowing to retrieve information about the size of the alveoli (or voids) and, thus, about possible defects of the lung.

Preferably, the processing means is adapted for generating an intensity decay image and/or a decay time image from the determined intensity of the signal decay or the determined signal decay time, respectively. Such an image provides and visually displays the additional information in which areas of the lung (or object) possible defects, e.g. enlarged alveoli, are present or in which areas the voids are larger (or smaller) as desired.

According to another embodiment the void size of voids within the object is determined by generating a first image and a second image from the first and second detection signals, in particular for the predetermined areas in the field of view, and for comparing said first and second images. Thus, the acquired detection signals are not compared directly, but images are first generated therefrom, which are then compared. Preferably, the images generated from the first and second detection signals and/or a difference image therefrom are displayed. It is also possible to use image (or pattern) recognition tools to automatically find unusual areas in the images, in particular in the difference image.

Generally, both alternative embodiments (first reconstructing images and then comparing the images, or generating an image from one or more signal decay times or decays of the signal intensity) are equally valuable and mathematically equivalent. It might be more illustrative for the user to first generate images and then determine a significant parameter, e.g. a signal decay time, therefrom. If signal can also be obtained from adsorbed particles, then the use of the detection signals might be better. Since in the second (and further) signal acquisitions it is already known, how many particles are adsorbed, the detection signal can be better fitted (using two system functions, one for particles in the aerosol and one for adsorbed particles).

It is also possible to determine such images only for predetermined areas, in particular for part of or all pulmonary alveoli. Even further, if by use of other methods, e.g. from another imaging modality or another diagnostic tool, there is a suspicion that a certain area might be defective, the signal acquisition and/or signal processing might be restricted to such an area to save time.

While the invention has been explained so far with reference to the acquisition of first and second detection signals, it is possible as well to determine the void size of voids within the object from a plurality of detection signals acquired after inhalation of the aerosol at subsequent moments in time. This enhances the accuracy of the retrieved information and provides more details of the void size in the various areas from which detection signals are acquired.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Before the details of the present invention shall be explained, basics of magnetic particle imaging shall be explained in detail with reference to FIGS. 1 to 4. In particular, two embodiments of an MPI scanner for medical diagnostics will be described. An informal description of the data acquisition is also given. The similarities and differences between the two embodiments will be pointed out.

Figure 1:
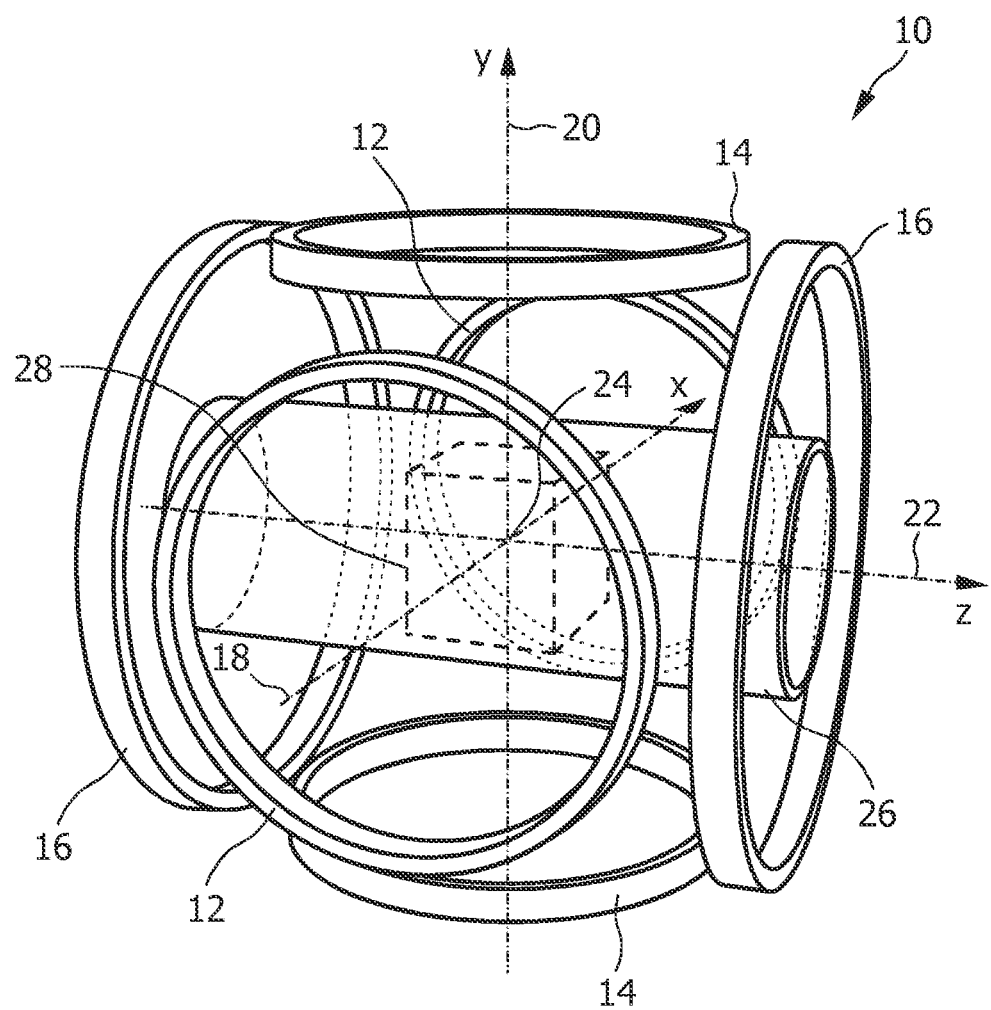
FIG. 1 shows a first embodiment of an MPI apparatus.

The first embodiment 10 of an MPI scanner shown in FIG. 1 has three prominent pairs 12, 14, 16 of coaxial parallel circular coils, each pair being arranged as illustrated in FIG. 1. These coil pairs 12, 14, 16 serve to generate the selection field as well as the drive and focus fields. The axes 18, 20, 22 of the three coil pairs 12, 14, 16 are mutually orthogonal and meet in a single point, designated the isocenter 24 of the MPI scanner 10. In addition, these axes 18, 20, 22 serve as the axes of a 3D Cartesian x-y-z coordinate system attached to the isocenter 24. The vertical axis 20 is nominated the y-axis, so that the x and z-axes are horizontal. The coil pairs 12, 14, 16 are also named after their axes. For example, the y-coil pair 14 is formed by the coils at the top and the bottom of the scanner. Moreover, the coil with the positive (negative) y-coordinate is called the $y^+$-coil ($y^-$-coil), and similarly for the remaining coils.

The scanner 10 can be set to direct a predetermined, time dependent electric current through each of these coils 12, 14, 16, and in either direction. If the current flows clockwise around a coil when seen along this coil's axis, it will be taken as positive, otherwise as negative. To generate the static selection field, a constant positive current $I^S$ is made to flow through the $z^+$-coil, and the current $-I^S$ is made to flow through the $z^-$-coil. The z-coil pair 16 then acts as an antiparallel circular coil pair.

Figure 2:
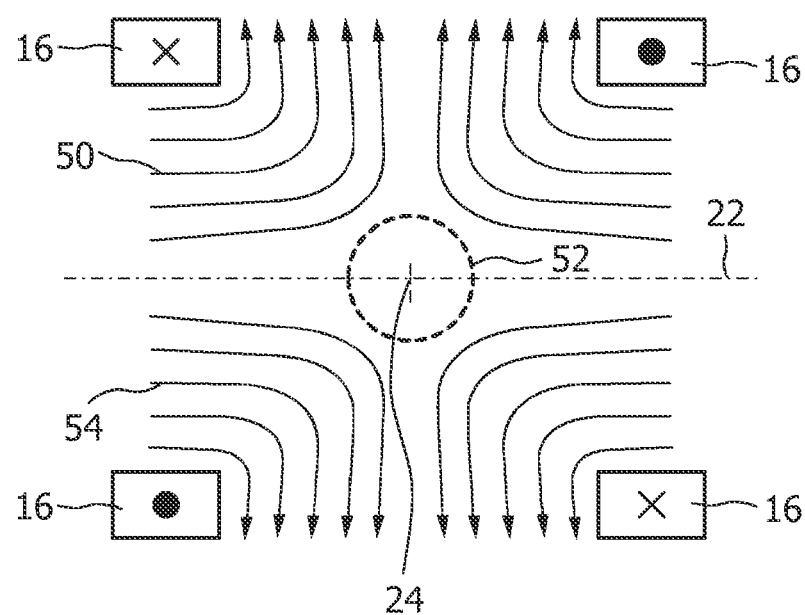
FIG. 2 shows an example of the selection field pattern produced by an apparatus as shown in FIG. 1.

The magnetic selection field which is generally a gradient magnetic field is represented in FIG. 2 by the field lines 50. It has a substantially constant gradient in the direction of the (e.g. horizontal) z-axis 22 of the z-coil pair 16 generating the selection field and reaches the value zero in the isocenter 24 on this axis 22. Starting from this field-free point (not individually shown in FIG. 2), the field strength of the magnetic selection field 50 increases in all three spatial directions as the distance increases from the field-free point. In a first sub-zone or region 52 which is denoted by a dashed line around the isocenter 24 the field strength is so small that the magnetization of particles present in that first sub-zone 52 is not saturated, whereas the magnetization of particles present in a second sub-zone 54 (outside the region 52) is in a state of saturation. The field-free point or first sub-zone 52 of the scanner's field of view 28 is preferably a spatially coherent area; it may also be a punctiform area, a line or a flat area. In the second sub-zone 54 (i.e. in the residual part of the scanner's field of view 28 outside of the first sub-zone 52) the magnetic field strength of the selection field is sufficiently strong to keep the magnetic particles in a state of saturation.

By changing the position of the two sub-zones 52, 54 within the field of view 28, the (overall) magnetization in the field of view 28 changes. By measuring the magnetization in the field of view 28 or physical parameters influenced by the magnetization, information about the spatial distribution of the magnetic particles in the field of view 28 can be obtained. In order to change the relative spatial position of the two sub-zones 52, 54 in the field of view 28, further magnetic fields, i.e. the magnetic drive field, and, if applicable, the magnetic focus field, are superposed to the selection field 50 in the field of view 28 or at least in a part of the field of view 28.

To generate the drive field, a time dependent current $I^D_1$ is made to flow through both x-coils 12, a time dependent current $I^D_2$ through both y-coils 14, and a time dependent current $I^D_3$ through both z-coils 16. Thus, each of the three coil pairs acts as a parallel circular coil pair. Similarly, to generate the focus field, a time dependent current $I^F_1$ is made to flow through both x-coils 12, a current $I^F_2$ through both y-coils 14, and a current $I^F_3$ through both z-coils 16.

It should be noted that the z-coil pair 16 is special: It generates not only its share of the drive and focus fields, but also the selection field. The current flowing through the $z^\pm$-coil is $I^D_3 + I^F_3 + I^S$. The current flowing through the remaining two coil pairs 12, 14 is $I^D_k + I^F_k$, k=1, 2. Because of their geometry and symmetry, the three coil pairs 12, 14, 16 are well decoupled. This is wanted.

Being generated by an anti-parallel circular coil pair, the selection field is rotationally symmetric about the z-axis, and its z-component is nearly linear in z and independent of x and y in a sizeable volume around the isocenter 24. In particular, the selection field has a single field free point (FFP) at the isocenter. In contrast, the contributions to the drive and focus fields, which are generated by parallel circular coil pairs, are spatially nearly homogeneous in a sizeable volume around the isocenter 24 and parallel to the axis of the respective coil pair. The drive and focus fields jointly generated by all three parallel circular coil pairs are spatially nearly homogeneous and can be given any direction and strength, up to some maximum strength. The drive and focus fields are also time dependent. The difference between the focus field and the drive field is that the focus field varies slowly in time and has a large amplitude while the drive field varies rapidly and has a small amplitude. There are physical and biomedical reasons to treat these fields differently. A rapidly varying field with a large amplitude would be difficult to generate and hazardous to the patient.

The embodiment 10 of the MPI scanner has at least one further pair, preferably three further pairs, of parallel circular coils, again oriented along the x-, y-, and z-axes. These coil pairs, which are not shown in FIG. 1, serve as receive coils. As with the coil pairs 12, 14, 16 for the drive and focus fields, the magnetic field generated by a constant current flowing through one of these receive coil pairs is spatially nearly homogeneous within the field of view and parallel to the axis of the respective coil pair. The receive coils are supposed to be well decoupled. The time dependent voltage induced in a receive coil is amplified and sampled by a receiver attached to this coil. More precisely, to cope with the enormous dynamic range of this signal, the receiver samples the difference between the received signal and a reference signal. The transfer function of the receiver is non-zero from DC up to the point where the expected signal level drops below the noise level.

The embodiment 10 of the MPI scanner shown in FIG. 1 has a cylindrical bore 26 along the z-axis 22, i.e. along the axis of the selection field. All coils are placed outside this bore 26. For the data acquisition, the patient (or object) to be imaged (or treated) is placed in the bore 26 such that the patient's volume of interest—that volume of the patient (or object) that shall be imaged (or treated)—is enclosed by the scanner's field of view 28—that volume of the scanner whose contents the scanner can image. The patient (or object) is, for instance, placed on a patient table. The field of view 28 is a geometrically simple, isocentric volume in the interior of the bore 26, such as a cube, a ball, or a cylinder. A cubical field of view 28 is illustrated in FIG. 1.

The size of the first sub-zone 52 is dependent on the one hand on the strength of the gradient of the magnetic selection field and on the other hand on the field strength of the magnetic field required for saturation. For a sufficient saturation of the magnetic particles at a magnetic field strength of 80 A/m and a gradient (in a given space direction) of the field strength of the magnetic selection field amounting to $50 \times 10^3$ A/m$^2$, the first sub-zone 52 in which the magnetization of the particles is not saturated has dimensions of about 1 mm (in the given space direction).

The patient's volume of interest is supposed to contain magnetic nanoparticles 199. Especially prior to therapeutic and/or diagnostic treatment of, for example, a tumor, the magnetic particles are positioned in the volume of interest, e.g. by means of a liquid comprising the magnetic particles which is injected into the body of the patient (object) or otherwise administered, e.g. orally, to the patient.

An embodiment of magnetic particles comprises, for example, a spherical substrate, for example, of glass which is provided with a soft-magnetic layer which has a thickness of, for example, 5 nm and consists, for example, of an iron-nickel alloy (for example, Permalloy). This layer may be covered, for example, by means of a coating layer which protects the particle against chemically and/or physically aggressive environments, e.g. acids. The magnetic field strength of the magnetic selection field 50 required for the saturation of the magnetization of such particles is dependent on various parameters, e.g. the diameter of the particles, the used magnetic material for the magnetic layer and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating of a material having a lower saturation magnetization is chosen or when the thickness of the layer is reduced. Magnetic particles that can generally be used are available on the market under the trade name Resovist.

For further details of the generally usable magnetic particles and particle compositions, the corresponding parts of EP 1304542, WO 2004/091386, WO 2004/091390, WO 2004/091394, WO 2004/091395, WO 2004/091396, WO 2004/091397, WO 2004/091398, WO 2004/091408 are herewith referred to, which are herein incorporated by reference. In these documents more details of the MPI method in general can be found as well.

The data acquisition starts at time $t_s$ and ends at time $t_e$. During the data acquisition, the x-, y-, and z-coil pairs 12, 14, 16 generate a position—and time dependent magnetic field, the applied field. This is achieved by directing suitable currents through the coils. In effect, the drive and focus fields push the selection field around such that the FFP moves along a preselected FFP trajectory that traces out the volume of scanning—a superset of the field of view. The applied field orientates the magnetic nanoparticles in the patient. As the applied field changes, the resulting magnetization changes too, though it responds nonlinearly to the applied field. The sum of the changing applied field and the changing magnetization induces a time dependent voltage $V_k$ across the terminals of receive coil pair along the $x_k$-axis. The associated receiver converts this voltage to a signal $S_k(t)$, which it samples and outputs.

It is advantageous to receive or to detect signals from the magnetic particles located in the first sub-zone 52 in another frequency band (shifted to higher frequencies) than the frequency band of the magnetic drive field variations. This is possible because frequency components of higher harmonics of the magnetic drive field frequency occur due to a change in magnetization of the magnetic particles in the scanner's field of view 28 as a result of the non-linearity of the magnetization characteristics.

Figure 3:
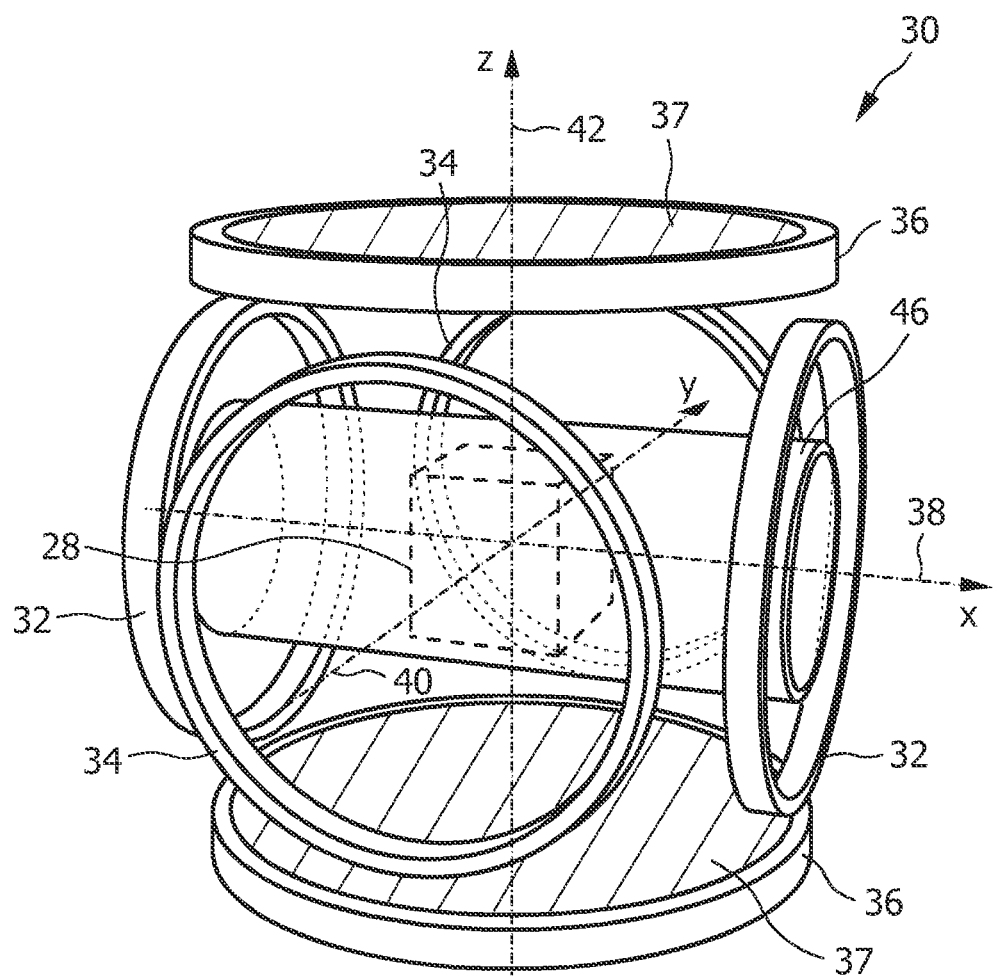
FIG. 3 shows a first embodiment of an MPI apparatus.

Like the first embodiment 10 shown in FIG. 1, the second embodiment 30 of the MPI scanner shown in FIG. 3 has three circular and mutually orthogonal coil pairs 32, 34, 36, but these coil pairs 32, 34, 36 generate the selection field and the focus field only. The z-coils 36, which again generate the selection field, are filled with ferromagnetic material 37. The z-axis 42 of this embodiment 30 is oriented vertically, while the x- and y-axes 38, 40 are oriented horizontally. The bore 46 of the scanner is parallel to the x-axis 38 and, thus, perpendicular to the axis 42 of the selection field. The drive field is generated by a solenoid (not shown) along the x-axis 38 and by pairs of saddle coils (not shown) along the two remaining axes 40, 42. These coils are wound around a tube which forms the bore. The drive field coils also serve as receive coils. The signals picked up by the receive coils are sent through a high-pass filter that suppresses the contribution caused by the applied field.

To give a few typical parameters of such an embodiment: The z-gradient of the selection field, G, has a strength of $G/\mu_0=2.5$ T/m, where $\mu_0$ is the vacuum permeability. The selection field generated does either not vary at all over the time or the variation is comparably slow, preferably between approximately 1 Hz and approximately 100 Hz. The temporal frequency spectrum of the drive field is concentrated in a narrow band around 25 kHz (up to approximately 100 kHz). The useful frequency spectrum of the received signals lies between 50 kHz and 1 MHz (eventually up to approximately 10 MHz). The bore has a diameter of 120 mm. The biggest cube 48 that fits into the bore 46 has an edge length of 120 mm/$\sqrt{2}\approx$84 mm.

As shown in the above embodiments the various magnetic fields can be generated by coils of the same coils pairs and by providing these coils with appropriately generated currents. However, and especially for the purpose of a signal interpretation with a higher signal to noise ratio, it may be advantageous when the temporally constant (or quasi constant) selection field and the temporally variable drive field and focus field are generated by separate coil pairs. Generally, coil pairs of the Helmholtz type can be used for these coils, which are generally known, e.g. from the field of magnetic resonance apparatus with open magnets (open MRI) in which a radio frequency (RF) coil pair is situated above and below the region of interest, said RF coil pair being capable of generating a temporally variable magnetic field. Therefore, the construction of such coils need not be further elaborated herein.

In an alternative embodiment for the generation of the selection field, permanent magnets (not shown) can be used. In the space between two poles of such (opposing) permanent magnets (not shown) there is formed a magnetic field which is similar to that shown in FIG. 2, that is, when the opposing poles have the same polarity. In another alternative embodiment, the selection field can be generated by a mixture of at least one permanent magnet and at least one coil.

Figure 4:
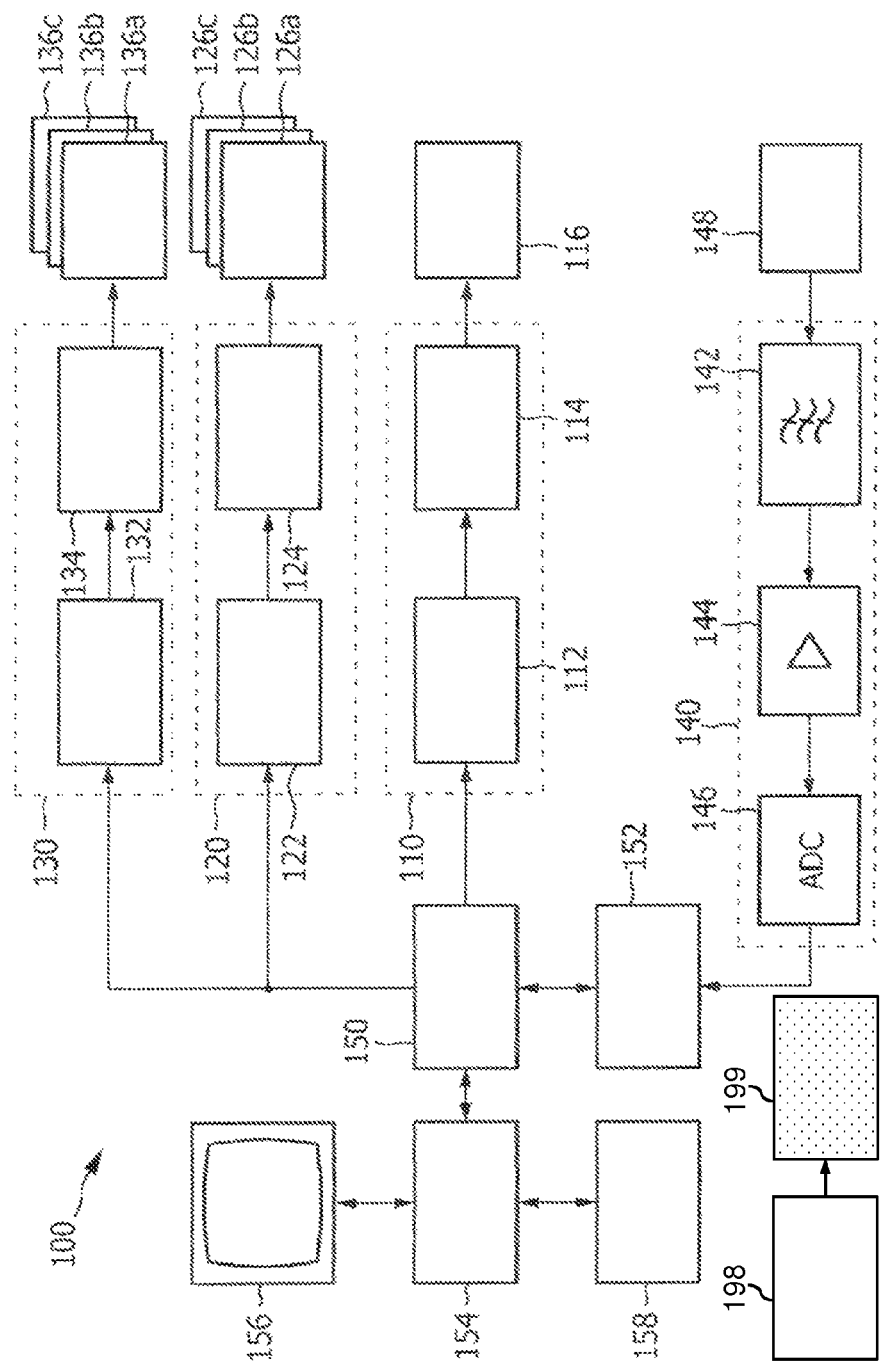
FIG. 4 shows a block diagram of an MPI apparatus according to the present invention.

FIG. 4 shows a general block diagram of an MPI apparatus 10 according to the present invention. The general principles of magnetic particle imaging and of magnetic resonance imaging explained above are valid and applicable to this embodiment as well, unless otherwise specified.

The embodiment of the apparatus 100 shown in FIG. 4 comprises a set of various coils for generating the desired magnetic fields. First, the coils and their functions in a MPI mode shall be explained.

For generating the magnetic (gradient) selection field explained above, selection means are provided comprising a set of selection field (SF) coils 116, preferably comprising at least one pair of coil elements. The selection means further comprises a selection field signal generator unit 110. Preferably, a separate generator subunit is provided for each coil element (or each pair of coil elements) of the set 116 of selection field coils. Said selection field signal generator unit 110 comprises a controllable selection field current source 112 (generally including an amplifier) and a filter unit 114 which provide the respective section field coil element with the selection field current to individually set the gradient strength of the selection field in the desired direction. Preferably, a DC current is provided. If the selection field coil elements are arranged as opposed coils, e.g. on opposite sides of the field of view, the selection field currents of opposed coils are preferably oppositely oriented.

The selection field signal generator unit 110 is controlled by a control unit 150, which preferably controls the selection field current generation 110 such that the sum of the field strength and the sum of the gradient strength of all spatial fractions of the selection field is maintained at a predefined level.

For generation of a magnetic focus field the apparatus 100 further comprises focus means comprising a set of focus field (FF) coils, preferably comprising three pairs 126a, 126b, 126c of oppositely arranged focus field coil elements. Said magnetic focus field is generally used for changing the position in space of the region of action. The focus field coils are controlled by a focus field signal generator unit 120, preferably comprising a separate focus field signal generation subunit for each coil element (or at least each pair of coil elements) of said set of focus field coils. Said focus field signal generator unit 120 comprises a focus field current source 122 (preferably comprising a current amplifier) and a filter unit 124 for providing a focus field current to the respective coil of said subset of coils 126a, 126b, 126c which shall be used for generating the magnetic focus field. The focus field current unit 120 is also controlled by the control unit 150.

For generation of the magnetic drive field the apparatus 100 further comprises drive means comprising a subset of drive field (DF) coils, preferably comprising three pairs 136a, 136b, 136c of oppositely arranged drive field coil elements. The drive field coils are controlled by a drive field signal generator unit 130, preferably comprising a separate drive field signal generation subunit for each coil element (or at least each pair of coil elements) of said set of drive field coils. Said drive field signal generator unit 130 comprises a drive field current source 41 (preferably including a current amplifier) and a filter unit 42 for providing a drive field current to the respective drive field coil. The drive field current source 41 is adapted for generating an AC current and is also controlled by the control unit 150.

For signal detection receiving means 148, in particular a receiving coil, and a signal receiving unit 140, which receives signals detected by said receiving means 148, are provided. Said signal receiving unit 140 comprises a filter unit 142 for filtering the received detection signals. The aim of this filtering is to separate measured values, which are caused by the magnetization in the examination area which is influenced by the change in position of the two part-regions (52, 54), from other, interfering signals. To this end, the filter unit 142 may be designed for example such that signals which have temporal frequencies that are smaller than the temporal frequencies with which the receiving coil 148 is operated, or smaller than twice these temporal frequencies, do not pass the filter unit 142. The signals are then transmitted via an amplifier unit 144 to an analog/digital converter 146 (ADC). The digitalized signals produced by the analog/digital converter 146 are fed to an image processing unit (also called reconstruction means) 152, which reconstructs the spatial distribution of the magnetic particles from these signals and the respective position which the first part-region 52 of the first magnetic field in the examination area assumed during receipt of the respective signal and which the image processing unit 152 obtains from the control unit 150. The reconstructed spatial distribution of the magnetic particles is finally transmitted via the control means 150 to a computer 154, which displays it on a monitor 156. Thus, an image can be displayed showing the distribution of magnetic particles in the field of view of the examination area.

Further, an input unit 158 is provided, for example a keyboard. A user is therefore able to set the desired direction of the highest resolution and in turn receives the respective image of the region of action on the monitor 156. If the critical direction, in which the highest resolution is needed, deviates from the direction set first by the user, the user can still vary the direction manually in order to produce a further image with an improved imaging resolution. This resolution improvement process can also be operated automatically by the control unit 150 and the computer 154. The control unit 150 in this embodiment sets the gradient field in a first direction which is automatically estimated or set as start value by the user. The direction of the gradient field is then varied stepwise until the resolution of the thereby received images, which are compared by the computer 154, is maximal, respectively not improved anymore. The most critical direction can therefore be found respectively adapted automatically in order to receive the highest possible resolution.

In the following, the details of the present invention will be explained with based on an embodiment for determining (or at least estimating) the size (or at least mean size) of alveoli in a patient's lung. The invention is, however, neither restricted to such an embodiment, nor to the determination of the size of alveoli.

To determine the size of alveoli of a patient having inhaled an aerosol containing magnetic particles, the computer (or, more generally, processing means) 154 is adapted for determining the size of alveoli from first detection signals acquired directly after inhalation of the aerosol and second detection signals acquired after a time duration after inhalation of the aerosol. The control unit 150 thus controls the various signal generation means 110, 120, 130 to generate and provide appropriate control currents to the respective coils 116, 126, 136 so that they generate magnetic fields by which the field free point (FFP) 52 (i.e. the first sub-region) is moved along a predetermined trajectory through a region of interest in the field of view 28. During this movement of the FFP 52 the detection signals are acquired which are thereafter processed and evaluated by the computer 154. This FFP movement is done at least twice, preferably along the same trajectory, and detection signals are acquired at least twice from the same region of interest (and, preferably, from the same locations within the region of interest). Thereby, the first FFP movement and signal acquisition is done immediately or shortly (generally not more than 5 seconds) after the inhalation of the aerosol, and the second FFP movement and signal acquisition is done a short time (e.g. 1 to 5 seconds) after the first FFP movement and signal acquisition. Preferably, the signal acquisition is already started during the inhalation, and the first data set (or image reconstructed therefrom) is used as first (reference) data set. For obtaining a full data set of detection signals of the lung, 0.5 to 1 second should be sufficient.

The invention is based on the idea that the inhaled aerosol comprises very small magnetic nano-particles which are able to diffuse within the alveoli after inhalation. If they reach the surface of the alveoli, they remain attached to the surface and have a reduced viscosity compared to the previous state when they diffuse within the alveoli. This, however, means that from magnetic particles that are attached to the surface of the alveoli, a lower detection signal is emitted (and detected by the receiving coil 148) compared to magnetic particles that are freely diffusing within the alveoli from which a higher detection signal can be obtained.

This knowledge is exploited according to the present invention by evaluating the at least two sets of detection signals acquired at different moments in time after inhalation of the magnetic particles. Since the second detection signals are required when at least part of the magnetic particles are already attached to the surface of the alveoli, lower signal intensities are expected. The amount of the drop in signal intensity and/or the signal decay time, however, depends on the size of the alveoli. In particular, if the alveoli are enlarged, as is the case for emphysema, it takes a longer time until the magnetic particles diffuse up to the alveoli's surface, whereas this time is shorter for smaller (healthy) alveoli. In other words, if there is a large diffusion and a slow signal decay time, this is an indication for enlarged alveoli and, thus, for emphysema.

The computer 154 is thus adapted for appropriately evaluating the acquired detection signals, for instance by comparing the detection signals, in particular the signal decay time and/or the signal intensities. It is also possible to determine images from both sets of detection signals separately and thereafter to generate a difference image which can give information about the areas with defective alveoli.

Figure 5A:
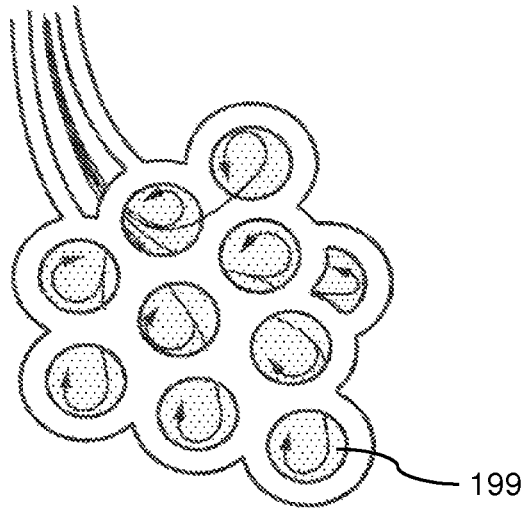
FIG. 5 shows a healthy alveolus and an emphysematic alveolus.
Figure 5B:
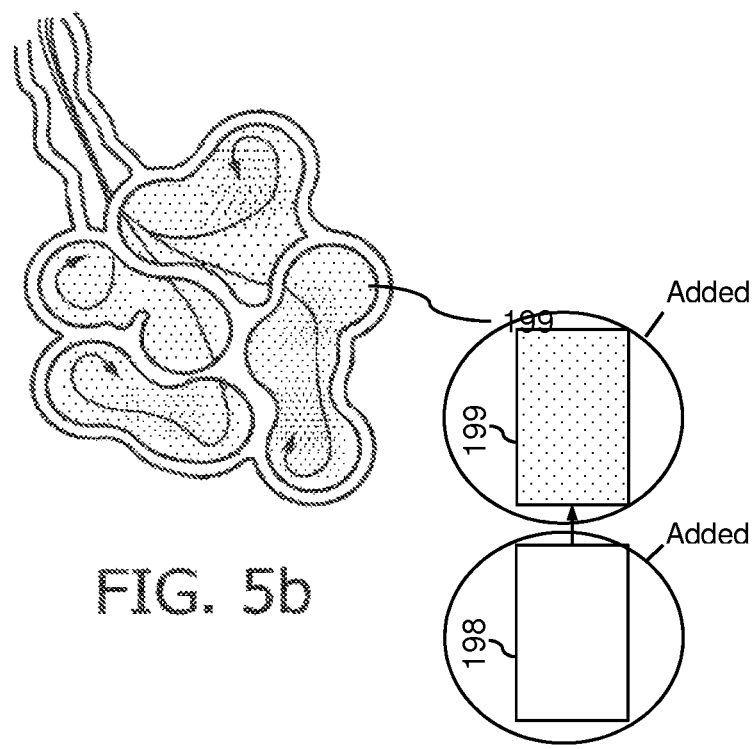

As mentioned, the invention can be applied to determine whether or not there is emphysema. As shown in FIG. 5, an emphysematic alveolus (FIG. 5b) is enlarged compared to a healthy alveolus (FIG. 5a).

The invention can further be applied to determine whether or not the patient suffers from asthma, in which the airways of the lung are inflamed (swollen), or suffers from chronic obstructive pulmonary disease (COPD) in which the airways and air sacs loose their elastic quality, the walls between many of the air sacs are destroyed, the walls of the airways become thick and inflamed (swollen) and/or the airways make more mucus than usual, which tends to clog the airways.

Using the present invention, it is thus mainly possible to get information about the average size of hollow structures, like alveoli, which might give indications on COPD. Together with further information on less or delayed ventilized areas, which might not show increased alveoli, or movement profiles of the lung, e.g. to see hardenings, obtained by other methods, this allows an improved diagnosis or control of a therapy. The main essential effect of the present invention thus is to provide the ability to determine the (average) size of alveoli or, more generally, of voids in an object.

While in the most simple embodiment two sets of detection signals are required at subsequent times after inhalation of the aerosol (each set being acquired during movement of the FFP along a trajectory), it is also possible to acquire more sets of detection signals at subsequent times, e.g. 10 detection signals, wherein a detection signal is acquired every 200 ms. This provides more information and enhances the accuracy of the achieved results.

The aerosol containing the (very) fine magnetic particles can be produced by a spraying process. Ideally, there are only individual particles. Therefore, high pressure devices or an electro-spray mechanism 198 could be used. To assist the formation of fine particles it is beneficial, if a sufficient low initial particle concentration is used such that only one particle is in one droplet. The, the water is evaporated using a mixing with dry air and heating to body temperature. To achieve a fine spray, the amount of air needed for the evaporation may result in a too low particle concentration. This problem can be solved by concentrating the aerosol particles in spinning air vortexes by centrifugal forces.

The apparent diffusion coefficient is preferably calculated using a computer program evaluating the acquired detection signals, e.g. the decay and change of the detection signals in air space. Alternatively, the time constant of the signal decay may be plotted directly.

As illustrated above, the present invention proposes to use for ventilation measurement. An aerosol of a magnetic nanoparticle suspension, in particular a nano-spray, has to be inhaled by the patient for assessing the diffusion in the lung. Using suitable magnetic particles, a difference in the signature of the aerosol and adsorbed particles can be imaged. The apparent diffusion coefficient is calculated evaluating the detection signals acquired subsequently after inhalation of the aerosol. For instance, the time constant per particle adsorption in the lung tissue can be determined.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. An apparatus (100) for void size determination of voids within an object into which an aerosol containing magnetic particles has been introduced, which apparatus comprises:
   selection means comprising a selection field signal generator unit (110) and selection field coils (116) for generating a magnetic selection field (50) having a pattern in space of its magnetic field strength such that a first sub-zone (52) having a low magnetic field strength and a second sub-zone (54) having a higher magnetic field strength are formed in a field of view (28),
   drive means comprising drive field signal generator units (130) and drive field coils (136a, 136b, 136c) for changing the position in space of the two sub-zones (52, 54) in the field of view (28) by means of a magnetic drive field so that the magnetization of the magnetic material changes locally,
   receiving means comprising at least one signal receiving unit (140) and at least one receiving coil (148) for acquiring detection signals, which detection signals depend on the magnetization in the field of view (28), which magnetization is influenced by the change in the position in space of the first and second sub-zone (52, 54), and
   processing means (154) for determining the void size of voids within the object from a first one of the detection signals acquired directly after introduction of the aerosol and a second one of the detection signals acquired after a time duration after introduction of the aerosol.

2. An apparatus (100) as claimed in claim 1, wherein said processing means (154) is adapted for determining the void size of voids within the object by comparing the first and second detection signals, in particular for predetermined areas in the field of view (28).

3. An apparatus (100) as claimed in claim 2, wherein said processing means (154) is adapted for determining the void size of voids within the object by determining the intensity of the signal decay from the comparison of the first and second detection signals, in particular for the predetermined areas in the field of view (28).

4. An apparatus (100) as claimed in claim 2, wherein said processing means (154) is adapted for determining the void size of voids within the object by determining the signal decay time from the comparison of the first and second detection signals, in particular for the predetermined areas in the field of view (28).

5. An apparatus (100) as claimed in claim 3, wherein said processing means (154) is adapted for generating an intensity decay image and/or a decay time image from the determined intensity of the signal decay or the determined signal decay time, respectively.

6. An apparatus (100) as claimed in claim 1, wherein said processing means (154) is adapted for determining the void size of voids within the object by generating a first image and a second image from the first and second detection signals, in particular for the predetermined areas in the field of view (28), and for comparing said first and second images.

7. An apparatus (100) as claimed in claim 6, wherein said processing means (154) is adapted for generating a difference image from a position-dependent subtraction between the first image and the second image, in particular for the predetermined areas in the field of view (28).

8. An apparatus (100) as claimed in claim 2, wherein said predetermined areas are a single or a group of voids.

9. An apparatus (100) as claimed in claim 1, wherein said processing means (154) is adapted for determining the void size of voids within the object from a plurality of detection signals acquired after introduction of the aerosol at subsequent moments in time.

10. An apparatus (100) as claimed in claim 1, further comprising an aerosol generator for generating an aerosol containing singularized magnetic particles.

11. A method for void size determination of voids within an object into which an aerosol containing magnetic particles has been introduced, which method comprises the steps of:
   generating a magnetic selection field (50) having a pattern in space of its magnetic field strength such that a first sub-zone (52) having a low magnetic field strength and a second sub-zone (54) having a higher magnetic field strength are formed in a field of view (28) by selection means comprising a selection field signal generator unit (110) and selection field generation elements (116), changing the position in space of the two sub-zones (52, 54) in the field of view (28) by means of a magnetic drive field so that the magnetization of the magnetic material changes locally by drive means comprising drive field signal generator units (130) and drive field coils (136*a*, 136*b*, 136*c*), acquiring detection signals, which detection signals depend on the magnetization in the field of view (28), which magnetization is influenced by the change in the position in space of the first and second sub-zone (52, 54), by receiving means comprising at least one signal receiving unit (140) and at least one receiving coil (148), and determining the void size of voids within the object from a first one of the detection signals acquired directly after introduction of the aerosol and a second one of the detection signals acquired after a time duration after introduction of the aerosol.

12. Computer program product comprising a non-transient comuter readable storage device having encoded thereon program code means for causing a computer to control an apparatus as claimed in claim 1 when said computer program is carried out on the computer.

* * * * *